United States Patent [19]

Tanzer

[11] Patent Number: 5,620,900
[45] Date of Patent: Apr. 15, 1997

[54] MEANS AND METHOD FOR THE DETERMINATION OF AMMONIUM IONS

[76] Inventor: Dieter Tanzer, c/o E. Merck Postfach 4119, D-64271 Darmstadt, Germany

[21] Appl. No.: 542,839

[22] Filed: Oct. 13, 1995

[30] Foreign Application Priority Data

Oct. 15, 1994 [DE] Germany .......................... 44 36 948.4

[51] Int. Cl.$^6$ .......................... G01N 33/00; G01N 21/77
[52] U.S. Cl. .......................... 436/113; 436/108; 436/111; 436/169; 422/55; 422/56; 435/12
[58] Field of Search .................. 422/55, 56, 99; 436/106, 108, 111, 113, 164, 169, 170; 435/12

[56] References Cited

U.S. PATENT DOCUMENTS

| | | | |
|---|---|---|---|
| 3,769,172 | 10/1973 | Bressler et al. ........................... | 435/12 |
| 4,194,063 | 3/1980 | Frank et al. ............................... | 435/12 |
| 4,223,089 | 9/1980 | Rothe et al. ............................... | 435/12 |
| 4,507,388 | 3/1985 | Tabacco et al. ........................... | 435/12 |
| 4,608,335 | 8/1986 | Fossati ...................................... | 435/12 |
| 4,710,458 | 12/1987 | Maines ...................................... | 435/12 |
| 5,258,314 | 11/1993 | Skerratt .................................... | 436/165 |

FOREIGN PATENT DOCUMENTS 0287112  10/1988  European Pat. Off. .

OTHER PUBLICATIONS

P.L. Searle, "The Berthelot or Indophenol Reaction and Its Use in the Analytical Chemistry of Nitrogen", *The Analyst*, vol. 109, pp. 549–568, May 1984.

C.J. Patton et al., "Spectrophotometric and Kinetics Investigation of the Berthelot Reaction for the Determination of Ammonia", vol. 49, pp. 464–469, Mar. 1977.

*Primary Examiner*—Jill Warden
*Assistant Examiner*—Maureen M. Wallenhorst
*Attorney, Agent, or Firm*—Millen, White, Zelano, & Branigan, P.C.

[57] ABSTRACT

The invention relates to an absorptive support and a method for the determination of ammonium ions in aqueous solutions by the Berthelot method using one absorptive support. The absorptive support is impregnated with a phenol derivative.

20 Claims, No Drawings

MEANS AND METHOD FOR THE DETERMINATION OF AMMONIUM IONS

The invention relates to a means and method for the determination of ammonium ions in aqueous solutions by the Berthelot method.

BACKGROUND OF THE INVENTION

The determination of the ammonium content has become a very important routine task of environmental analysis, particularly water analysis. The determination can here be carried out by three different methods:

- separating off the ammonia by distillation in an alkaline medium, followed by an acidimetric titration
- potentiometric determination using ion-selective electrodes or
- colorimetric or photometric determination after formation of a coloured compound.

The determinations based on colour formation have gained increasing importance in recent years. The colour reactions used here for ammonium ions are generally the methods of Nessler or Berthelot. Owing to the high detection sensitivity, the high selectivity and the relatively low susceptibility to interference, the Berthelot reaction in particular has become established as detection process for ammonium ions. The fields of application are manifold, e.g. determination of ammonium ions in water, food, soil extracts, biological materials, etc.

The formation of a blue colour on mixing ammonium ions, hypochlorite and phenol was described by Berthelot as early as 1859. The elucidation of the reaction mechanism was thereafter the subject of numerous studies (Anal. Chem. 49, 464 (1977)). A prerequisite for the reaction proceeding is a free para-position on the phenol used. Depending on the hypochloride source used and on the phenol component used, an optimum reaction requires adherence to characteristic reaction conditions such as pH and time sequence of the reagent additions. The phenol component used is generally phenol itself, salicylic acid and thymol. With regard to a high detection sensitivity and high reaction rate, a series of further phenol derivatives have been examined in detail in the prior art for their suitability for quantitative detection of ammonium ions. Among these, 2-methylphenol, 2,6-dimethylphenol, 2-chlorophenol, 2,6-dichlorophenol, guaiacol, o-phenylphenol, m-cresol, 1-naphthol and 2-methyl-5-hydroxyquinoline have, in particular, been found to be usable (Analyst 109, 549 (1984)).

There have been many attempts to optimize the Berthelot reaction by selection of suitable reagents and reaction conditions so as to make possible its use in continuous measurement systems and commercially available test kits. However, its use has hitherto remained the province of wet chemistry, i.e. for reactions in which liquid reactants are exclusively used.

Recently, however, analysis using solid absorptive supports, the so-called test strips, has gained increasing importance. The significant advantages of the use of test strips include, in particular, simple handling and unproblematical disposal owing to the small amounts of reagent. In these strips, all or part of the reagents necessary for the detection reaction are applied to absorptive or swellable supports or films. After contact of the reaction zone with the sample, the detection reaction proceeds. The colour detection reaction proceeds. The colour formed is a measure of the amount of analyte to be determined and can be evaluated visually with the aid of colour comparison scales or using simple reflectometers.

Test strips for detecting ammonium amounts based on the Nessler reaction are known, but they are suitable only for the detection of relatively high ammonium ion contents of more than 20 mg/l. Owing to the usually low ammonium ion contents of water samples, these can therefore frequently not be employed. Multilayer test strip systems exist for the determination of ammonium ions in blood plasma, but the detection in this system is based on the colour change of a pH indicator (bromophenol blue).

SUMMARY OF THE INVENTION

It is an object of the invention to provide a means and a method for the determination of ammonium ions in aqueous solutions by the Berthelot method, which is simple to use, sensitive and specific and is suitable for evaluation using a reflectometer.

Upon further study of the specification and appended claims, further objects and advantages of this invention will become apparent to those skilled in the art.

The invention provides a means for the determination of ammonium ions in aqueous solution by the Berthelot method, which is characterized in that it contains an absorptive support impregnated with an effective amount of a phenol derivative.

The invention further provides a method for the determination of ammonium ions in aqueous solutions by the Berthelot method, which is characterized in that an absorptive support impregnated with an effective amount of a phenol derivative is brought into contact with an alkaline sample solution containing a hypochlorite or a hypochlorite former (e.g., a compound able to generate hypochlorite or chlorine in aqueous solutions) and the colour change on the support is evaluated after a certain time.

It has been established that the phenols described in the prior art for the quantitative detection of ammonium ions are, for various reasons such as storage stability, detection sensitivity, reaction kinetics, undesired side reactions, colour stability of the indophenol formed, toxicity, reproducibility of the determination, etc., unsuitable for transferring the Berthelot reaction to a solid test support. In particular, those phenols most suitable in terms of colour formation and kinetics were too volatile and did not have the required affinity to the support material. This resulted, inter alia, in a more-or-less strong odour when the container used for storing the test strips was opened.

It has surprisingly been found that phenol derivatives such as hydroxyphenylalkyl alcohols, hydroxyphenolalkylcarboxylic acids and hydroxycinnamic acid, where the hydroxy group is in the 2 or 3-position and the alkyl group contains from 1 to 6 carbon atoms, are suitable for the means of the invention. Suitable phenol derivatives are, for example, hydroxybenzyl alcohol, hydroxyphenylacetic acid, hydroxycinnamic acid, 2-(2-hydroxyphenyl)ethanol, 2-(3-hydroxyphenyl)ethanol, 3-(2-hydroxyphenyl)propanol, 4-(2-hydroxyphenyl)butanol, 3-(2-hydroxyphenyl)propionic acid, 4-(2-hydroxyphenyl)butyric acid, 5-(2-hydyroxyphenyl)valeric acid. Preference is given to 2-hydroxybenzyl alcohol, 2-hydroxyphenylacetic acid and hydroxycinnamic acid, in particular 2-hydroxybenzyl alcohol. An impregnation solution containing a phenol derivative can contain, e.g., about 0.5–5%, preferably, 3.5%, of a phenol derivative. The absorptive supports of the invention which contain these compounds can be stored for more than one year at room temperature.

Absorptive supports which can be used are all those which are customarily used for such tests. Filter paper is most widely used, but it is also possible to use other absorptive cellulose or plastic products. For example, glass fiber can also be employed. The absorptive supports, preferably filter paper, are impregnated in a manner known per se with impregnation solutions which contain part of the reagents necessary for the determination of ammonium ions. The impregnated and dried papers can be made into square or rectangular zones which in turn can be adhesively bonded or sealed onto plastic films, paper strips or metal strips in a known manner.

The absorptive supports can also be applied in tape form to a plastic band prior to impregnation and after impregnation be cut vertically to the tape direction into handy strips.

It is advantageous for the absorptive support to contain not only the phenol derivative but also catalysts. If desired, the support can also contain complexing agent and buffer substances in effective amounts. Suitable catalysts are sodium nitroprusside, manganese(II) salts or zinc salts, preferably sodium nitroprusside. The impregnation solution can contain, e.g., about 0.05 to–0.2%, preferably 0.1%, of sodium nitroprusside.

The complexing agents and buffer substances mentioned can either be present on the absorptive support or be added to the sample solution. Addition to the sample solution has been found to be more advantageous.

To complex interfering substituents of the sample, the sample solution is admixed with, for example, 1-hydroxy-ethane-1,1-diphosphonic acid, cyclohexyldiaminotetracetic acid, citrate, EDTA, preferably 1-hydroxy-ethane-1,1-diphosphonic acid. The sample solution contains from about 2 to 10%, preferably 5%, of 1-hydroxyethane-1,1-diphosphonic acid.

To the sample solution are added buffer substances which can maintain a pH range of 10–12 and do not interfere with the detection reaction. Suitable buffer systems are those which can also be applied to the absorptive support. The buffer concentration to be employed depends on the pH of the sample solution and on the free acids or bases present therein. Suitable buffers are, for example, sodium hydroxide/tartrate buffer, sodium hydroxide/borate buffer, sodium carbonate/sodium hydrogen carbonate buffer, preferably sodium hydroxide/tartrate buffer.

The sample solution which has been brought to a pH of about 11 using the specified buffer systems is admixed with a hypochlorite or a hypochlorite former. Known hypochlorite formers which are suitable for this purpose are, for example, dichloroisocyanuric acid, trichloroisocyanuric acid, chloramine T and aqueous solutions of chlorine. Hypobromite can also be used in place of hypochlorite. According to the invention, preference is given to dichloroisocyanuric acid and sodium hypochlorite.

To carry out the determination of ammonium ions, the absorptive support is placed in the alkaline, hypochlorite-containing sample solution for about 2–20 minutes, preferably about 8 minutes, in such a way that the reaction zone is completely wetted. The test strip is then removed from the sample solution, shaken off vigorously and the coloration formed is evaluated using a reflectometer or by means of a colour comparison scale standard. The method of the invention makes possible, in contrast to known methods, a simple, accurate and rapid determination of ammonium ion in aqueous solutions by means of test strips, which allows concentrations of, e.g., about 0.2–20 mg/l to be determined.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding German application P 44 36 948.4, are hereby incorporated by reference.

EXAMPLE 1

A filter paper (Schöller & Hösch 300A) is impregnated with the following reagent solution and, after impregnation, dried using warm air:

| | |
|---|---|
| 3.5 g | of 2-hydroxybenzyl alcohol and |
| 0.1 g | of sodium nitroprusside |
| in 100 g | of water. |

The paper obtained is applied to a support material, e.g. polyester film, in a known manner.

Standard ammonium ion solutions having contents of from 0 to 10 mg/l, a pH of 11 and containing 1 mg of dichloroisocyanuric acid per 5 ml of solution are prepared. The test strips are placed in the solutions, removed after 8 minutes, shaken off and evaluated by measurement of the relative reflectivity using a simple reflectometer and by visual colorimetry.

The buffer solution for setting the pH contains

| | |
|---|---|
| 44 g | of potassium sodium tartrate, |
| 9 g | of NaOH pellets and |
| 5 g | of 1-hydroxyethane-1,1-diphosphonic acid sodium salt |
| in 100 g | of water. | a) Visual colorimetric evaluation:

| conc. [mg/l] | 0 | 0.5 | 2.5 | 5.0 | 10.0 |
|---|---|---|---|---|---|
| Color | color-less | pale green | turquoise | pale blue | blue |

The experiments show that various concentrations of ammonium ions produce significantly different colorations and can thus be determined by visual colorimetry with the aid of an appropriate colour scale.

b) Reflectometric evaluation

| conc. [mg/l] | 0 | 0.25 | 0.5 | 1.0 | 2.5 | 3.0 | 5.0 | 7.5 | 10.0 |
|---|---|---|---|---|---|---|---|---|---|
| rel. reflectivity [%] | 74.8 | 72.7 | 69.5 | 63.5 | 53.6 | 42.4 | 28.2 | 18.4 | 13.7 |

The reflectivity-concentration curve (calibration curve) measured above was read into a reflectometer by means of a bar code reading system and the relationship between concentration used and measured concentration was determined:

| conc. used [mg/l] | 0.5 | 1.0 | 2.5 | 6.5 |
|---|---|---|---|---|
| measured conc. [mg/l] | 0.5 | 1.0 | 2.5 | 6.2 |
| | 0.5 | 1.0 | 2.4 | 6.5 |
| | 0.5 | 0.9 | 2.5 | 6.6 |
| | 0.5 | 1.1 | 2.4 | 6.8 |
| | 0.5 | 1.0 | 2.6 | 6.3 |

As the results show, the sensitive reflectivity concentration curve combined with the high reproducibility of the detection reaction makes possible a very sensitive and precise determination of ammonium ions.

Analogous results are obtained if 2-hydroxyphenylacetic acid or hydroxycinnamic acid is used as phenyl derivative in place of 2-hydroxybenzyl alcohol.

EXAMPLE 2

Nine different wastewater samples are analyzed reflectometrically for ammonium ions using a method similar to Example 1. For comparison, the samples are analyzed by a conventional photometric method to give the following results:

| Sample | Reflectometry [mg/l] | Photometry [mg/l] |
|---|---|---|
| 1 | 3.8 | 3.5 |
| 2 | 4.6 | 4.8 |
| 3 | 4.9 | 5.1 |
| 4 | 2.6 | 2.4 |
| 5 | 4.6 | 4.5 |
| 6 | 4.2 | 4.1 |
| 7 | 0.5 | 0.4 |
| 8 | 0.6 | 0.6 |
| 9 | 0.6 | 0.7 |

The method using test strips makes possible, in contrast to existing methods, simple, accurate and rapid ammonium determination in aqueous sample solutions.

EXAMPLE 3

A filter paper (Schöller & Hösch 300A) is impregnated in succession with the following solutions and dried after each impregnation using warm air:

Solution 1:
  3.5 g of 2-hydyroxybenzyl alcohol and
  0.1 g of sodium nitroprusside in 100 g of water.

Solution 2:
  10 g of potassium sodium tartrate,
  2 g of NaOH pellets and
  1.1 g of 1-hydroxyethane-1,1-diphosphonic acid sodium salt in 100 g of water.

Detection is carried out as described in Example 1. Analogous results to those in Example 1 are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed:

1. A device for the determination of ammonium ions by the Berthelot method comprising, an absorptive support and a phenol derivative, wherein the phenol derivative is a hydroxyphenylalkyl alcohol, a hydroxyphenylalkylcarboxylic acid or a hydroxycinnamic acid, wherein the alkyl group contains 1–6 carbon atoms wherein the support is impregnated with an amount of the phenol derivative, which is effective to determine ammonium ion content by the Berthelot method and wherein the phenol derivative is suitable for performing the Berthelot method on the absorptive support.

2. A device according to claim 1, wherein the phenol derivative is hydroxybenzyl alcohol, hydroxyphenylacetic acid, or hydroxycinnamic acid, wherein the hydroxy group is in the 2 or 3 position.

3. A device according to claim 1, wherein the phenol derivative is 2-hydroxybenzyl alcohol.

4. A device according to claim 1, further comprising an amount of a catalyst which is effective to determine ammonium ion content by the Berthelot method, wherein the support is impregnated with the catalyst.

5. A device according to claim 4, wherein the catalyst is sodium nitroprusside.

6. A device according to claim 1, wherein the phenol derivative is 2-hydroxybenzyl alcohol, and the absorptive support is further impregnated with an amount of sodium nitroprusside which is effective as a catalyst in the Berhelot method.

7. A device according to claim 6, wherein the absorptive support is further impregnated with a complexing agent or buffer in amounts effective to determine ammonium ions in an aqueous solution by the Berthelot method.

8. A device according to claim 7, wherein the complexing agent is 1-hydroxyethane-1,1-diphosphonic acid, cyclohexyldiaminotetracetic acid, citrate, or EDTA.

9. A device according to claim 6, wherein the absorptive support is further impregnated with an amount of a complexing agent effective to determine ammonium ions in an aqueous solution by the Berthelot method.

10. A device according to claim 6, wherein the absorptive support is further impregnated with an amount of a buffer effective to determine ammonium ions in an aqueous solution by the Berthelot method.

11. A device according to claim 1, wherein the absorptive support is a filter paper.

12. A device according to claim 1, wherein the absorptive support further is impregnated with a complexing agent or buffer in amounts effective to determine ammonium ion content by the Berthelot method.

13. A device according to claim 12, wherein the complexing agent is 1-hydroxyethane-1,1-diphosphonic acid, cyclohexyldiaminotetracetic acid, titrate, or EDTA.

14. A method for the determination of ammonium ions in aqueous solutions by the Berthelot method, comprising contacting an absorptive support impregnated with an amount of a phenol derivative with an alkaline sample solution containing hypochlorite or a hypochlorite former, and identifying the resultant color change on the support, wherein the phenol derivative is a hydroxyphenylalkyl alcohol, a hydroxyphenylalkylcarboxylic acid or a hydroxycinnamic acid, wherein the alkyl group contains 1–6 carbon atoms and wherein the amount of said phenol derivative is effective to determine ammonium ions in an aqueous solution by the Berthelot method.

15. A method according to claim 14, wherein the phenol derivative is hydroxybenzyl alcohol, hydroxyphenylacetic acid, or hydroxycinnamic acid, wherein the hydroxy group is in the 2 or 3 position.

16. A method according to claim 14, wherein the phenol derivative is 2-hydroxybenzyl alcohol.

17. A method according to claim 14, wherein the absorptive support is further impregnated with an amount of a catalyst which is effective to determine ammonium ion content by the Berthelot method.

18. A method according to claim 14, wherein the phenol derivative is 2-hydroxybenzyl alcohol, and the absorptive support is further impregnated with an amount of sodium nitroprusside which is effective as a catalyst in the Berthelot method.

19. A device for the determination of ammonium ions by the Berthelot method comprising, an absorptive support impregnated with an effective amount of a phenol derivative, wherein the phenol derivative is a hydroxyphenylalkyl alcohol, a hydroxyphenylalkylcarboxylic acid, or a hydroxycinnamic acid, where the hydroxy group is in the 2- or 3-position and the alkyl group contains 1 to 6 carbon atoms, wherein the amount of the phenol derivative is effective for determining ammonium ion content by the Berthelot method, and wherein the phenol derivative is suitable for performing the Berthelot method on the absorptive support.

20. A device of claim 19, wherein the absorptive support is further impregnated with an amount of a catalyst which is effective for determining ammonium ion content by the Berthelot method.

* * * * *